United States Patent [19]

Suzuki et al.

[11] Patent Number: 5,478,550
[45] Date of Patent: Dec. 26, 1995

[54] ULTRAVIOLET-SHIELDING AGENT, METHOD FOR THE PREPARATION THEREOF AND COSMETIC COMPOSITION COMPOUNDED THEREWITH

[75] Inventors: Masao Suzuki; Sakae Yoshida, both of Saitama; Shigenobu Okamiya, Tokyo, all of Japan

[73] Assignee: Nippon Inorganic Colour & Chemical Co., Ltd., Tokyo, Japan

[21] Appl. No.: 128,078

[22] Filed: Sep. 29, 1993

[30] Foreign Application Priority Data

Nov. 6, 1992 [JP] Japan ................................. 4-322749
Nov. 6, 1992 [JP] Japan ................................. 4-322750

[51] Int. Cl.$^6$ .................. C01G 9/02; A61K 7/42; A61K 7/44
[52] U.S. Cl. ..................... 424/59; 423/623; 106/419
[58] Field of Search ..................... 423/623; 424/59; 106/419

[56] References Cited

FOREIGN PATENT DOCUMENTS

| 0220509 | 5/1987 | European Pat. Off. . |
|---|---|---|
| 0401045 | 12/1990 | European Pat. Off. . |
| 59-98009 | 6/1984 | Japan ................................. 423/623 |

OTHER PUBLICATIONS

WPIDS Abstract #92–345112 [42] of JP 042495848, 1992.
Database WPI Week 9242, *Derwent Publications Ltd.*, London, GB, AN 92–345112 & JP–A–4 249 584 (Tayca Co.) 4 Sep. 1992.

*Primary Examiner*—C. Warren Ivy
*Assistant Examiner*—D. Margaret M. Mach
*Attorney, Agent, or Firm*—Wenderoth, Lind & Ponack

[57] ABSTRACT

Disclosed is a novel ultraviolet-shielding agent in a powder form consisting of particles of an inorganic material having a specified refractive index and a flaky particle configuration, such as mica, talc, sericite and the like, compositely coated with a water-insoluble cerium compound and amorphous silica each in a specified coating amount. A method for the preparation of such an ultraviolet-shielding agent is disclosed. By virtue of the excellent ultraviolet-shielding effect along with good translucency as well as stability and safety against human skin, it is useful as an ultraviolet-shielding ingredient in cosmetic compositions.

7 Claims, 4 Drawing Sheets

ULTRAVIOLET-SHIELDING AGENT, METHOD FOR THE PREPARATION THEREOF AND COSMETIC COMPOSITION COMPOUNDED THEREWITH

BACKGROUND OF THE INVENTION

The present invention relates to an ultraviolet-shielding agent, a method for the preparation thereof and a cosmetic composition compounded therewith. More particularly, the invention relates to an ultraviolet-shielding agent based on a powdery inorganic material, a method for the preparation thereof and an ultraviolet-shielding cosmetic or toiletry composition compounded with the powdery ultraviolet-shielding agent.

As is well known, ultraviolet light as a constituent of sunlight has a strong influence on the living body to cause various undesirable changes, for example, in the human skin sometimes resulting in cutaneous cancers, and also has an influence to cause degradation of organic materials such as plastics. Accordingly, it is conventional that cosmetic or toiletry compositions to be applied to the human skin are compounded with an ultraviolet-absorbing or ultraviolet-shielding agent so as to protect the human skin from the direct influence of the ultraviolet light. Plastic resins are also compounded with an ultraviolet-absorbing or ultraviolet-shielding agent when shaped articles thereof are to be used in sunlight in order to mitigate ultraviolet-induced degradation thereof.

For example, cosmetic compositions, when desired to have a protecting effect against ultraviolet light, are sometimes compounded with an organic ultraviolet-absorbing agent capable of strongly absorbing ultraviolet light, such as oxybenzone and derivatives thereof, derivatives of salicylic acid, benzophenone compounds, derivatives of p-aminobenzoic acid, derivatives of cinnamic acid and the like. These organic ultraviolet-absorbing agents in general have good compatibility with organic ingredients in cosmetic compositions and plastic resins so that they are widely used when the material compounded therewith is desired to retain transparency or translucency.

Besides organic ultraviolet-absorbing agents such as those mentioned above, similar effects against ultraviolet light can be obtained by compounding a cosmetic composition or plastic resin with an ultraviolet-shielding agent which is an inorganic powder having an ability to scatter or diffuse ultraviolet light including zinc oxide, titanium dioxide, talc, clay and the like. In recent years, several organic compounds have been proposed to serve as an ultraviolet-shielding agent including 5-chlorouracil, guanine, cytosine and the like. Further, a proposal is made to use fine flakes of an iron-containing synthetic mica as an ultraviolet-shielding agent.

The above described ultraviolet-absorbing and ultraviolet-shielding agents each have their respective disadvantages and advantages. For example, the organic ultraviolet-absorbing and ultraviolet-shielding agents are generally not quite stable against irradiation with strong ultraviolet light so that no sustained protecting effect against ultraviolet light can be obtained therewith. In addition, some of these organic compounds have toxicity against the human body so that the application field thereof is more or less limited. Inorganic ultraviolet-shielding agents, on the other hand, also have various problems. Titanium dioxide has a high hiding power so that it cannot be compounded in a cosmetic composition or plastic resin desired to have good transparency or translucency although titanium dioxide has no toxicity against the human body. Some of inorganic ultraviolet-shielding agents have a catalytic activity to accelerate degradation of organic materials to decrease the durability of the material compounded therewith and also have an irritating effect on the human skin so that the amount thereof in a cosmetic composition is necessarily limited.

Accordingly, it is eagerly desired to develop a novel ultraviolet-shielding agent based on an inorganic powder free from the above described problems and disadvantages in the conventional inorganic ultraviolet-shielding agent as well as to develop a cosmetic composition capable of exhibiting an ultraviolet-shielding effect to the human skin without the problems and disadvantages in the prior art compositions.

SUMMARY OF THE INVENTION

The present invention accordingly has an object to provide a novel and improved ultraviolet-shielding agent based on an inorganic powder which can be compounded in various kinds of polymeric materials and cosmetic compositions with good dispersibility while only slightly decreasing the transparency or translucency of the composition compounded therewith, and having no toxicity against the human body and no catalytic activity to accelerate degradation of the material compounded therewith but having good stability and resistance against heat and chemicals, as well as a method for the preparation thereof.

The present invention also has an object to provide a novel cosmetic composition which can effectively protect human skin from the adverse influences of ultraviolet light without irritation to the skin and toxicity to the human body by compounding a novel inorganic ultraviolet-shielding agent.

Thus, the inorganic ultraviolet-shielding agent of the present invention is a powder consisting of particles of an inorganic material having a refractive index in the range from 1.45 to 1.65 and a flaky particle configuration, such as particles of mica, talc, sericite and the like, each particle being coated on the surface with a composite coating layer consisting of a water-insoluble cerium compound and amorphous silica after a calcination treatment at a specified temperature.

The above defined inorganic ultraviolet-shielding agent in a powdery form can be prepared by the method which comprises the steps of:

(A) dispersing particles of an inorganic material having a refractive index in the range from 1.45 to 1.65 and a flaky particle configuration in an aqueous medium to prepare an aqueous dispersion;

(B) adding, to the aqueous dispersion prepared in step (A) above, an aqueous solution of a water-soluble cerium compound;

(C) adding a precipitant of the cerium compound to the aqueous dispersion of the inorganic particles containing the water-soluble cerium compound so as to deposit a water-insoluble cerium compound on the surface of the particles;

(D) adding, to an aqueous dispersion of the inorganic particles having the water-insoluble cerium compound deposited on the surface thereof prepared in step (C), an aqueous solution of a water-soluble or water-dispersible silicate compound;

(E) adjusting the pH of the aqueous dispersion to 9 to 11 so as to deposit amorphous silica on the surface of the particles to form a composite coating layer consisting of the water-insoluble cerium compound and the amorphous silica;

(F) separating the particles from the aqueous medium of the dispersion followed by drying; and (G) calcining the dried particles at a temperature in the range from 200° to 1000° C.

Further, the cosmetic composition of the present invention is characterized by comprising, besides components constituting a cosmetic composition in admixture, an ultraviolet-shielding agent in the form of a powder consisting of particles of an inorganic material having a specified refractive index and a flaky particle configuration, each particle being coated with a composite coating layer consisting of a water-insoluble cerium compound and amorphous silica, in such an amount as to substantially shield ultraviolet light.

DETAILED DESCRIPTION OF THE PREFERRED EMBODIMENTS

Figure 1:
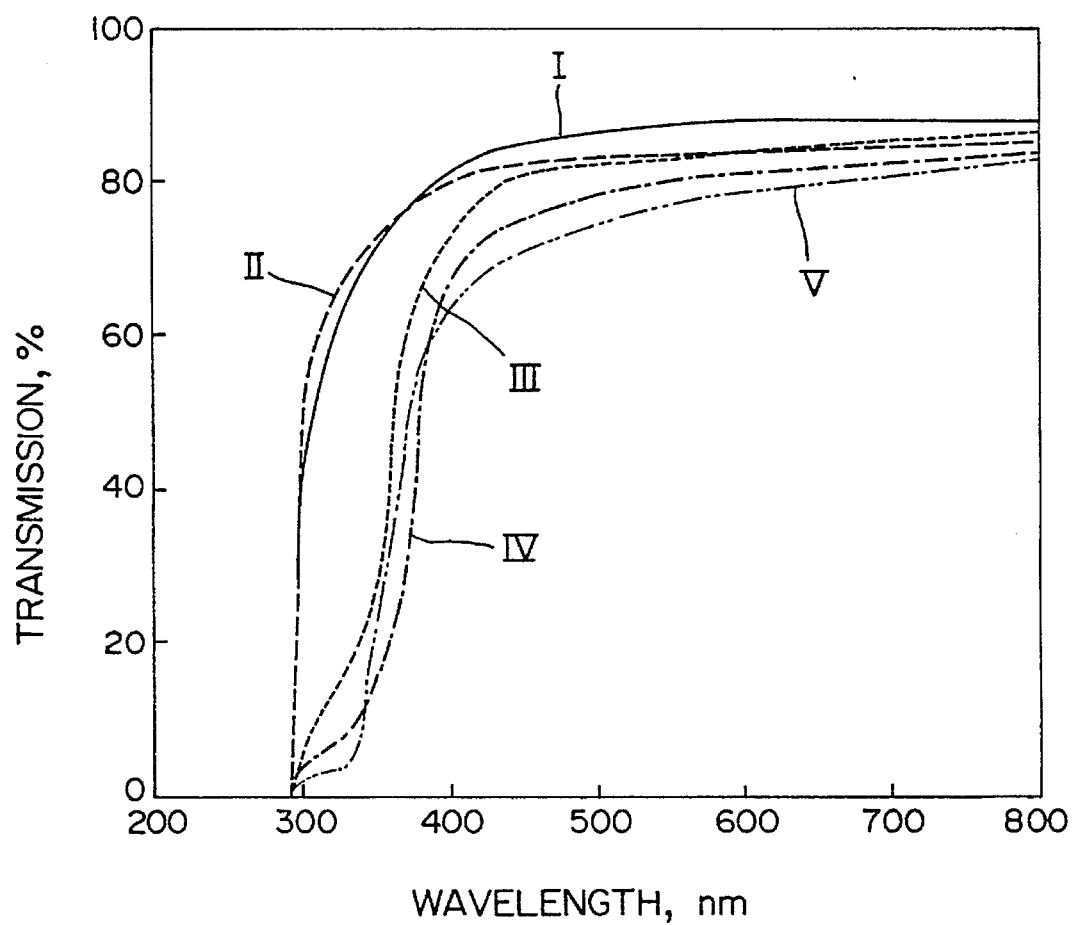
FIG. 1 is a graph showing transmission of light as a function of wavelength of light through layers of several ultraviolet-shielding agents prepared under varied calcination conditions.

As is described above, the ultraviolet-shielding agent of the present invention is a powder consisting of particles of an inorganic material having a specified refractive index and a flaky particle configuration, of which each particle is coated with a composite coating layer consisting of a water-insoluble cerium compound and amorphous silica.

It is known that cerium (IV) oxide and other cerium (IV) compounds have strong absorption of ultraviolet light so that cerium compounds are sometimes used when an ultraviolet-shielding effect is desired. For example, eyeglass lenses are prepared from optical glass containing cerium (IV) oxide as a constituent in order to protect the wearer's eyes against adverse influences of ultraviolet light. Further, it is known that certain colored pigments such as chrome yellow can be imparted with improved fastness against irradiation with ultraviolet light by the treatment with a water-soluble cerium salt such as cerium (IV) nitrate. The present invention has been completed as a result of the extensive investigations undertaken by the inventors on the basis of this knowledge in the prior art.

The starting material for the preparation of the inventive ultraviolet-shielding agent is a powder of an inorganic material consisting of particles having a flaky particle configuration and a refractive index in the range from 1.45 to 1.65 or, preferably, from 1.5 to 1.6 such as mica, talc, sericite and the like though not particularly limitative thereto. The flaky particle configuration here implied can be defined, for example, in terms of the so-called aspect ratio which should preferably be in the range from 10 to 100. In the first step of the preparation process of the inventive ultraviolet-shielding agent, the starting powder is dispersed in an aqueous medium by using a suitable blending machine to give an aqueous dispersion of the powder. The amount of water as the dispersion medium is not particularly limitative but, preferably, water is added to the pigment particles in such an amount that the aqueous dispersion contains from 5 to 40% by weight of the pigment particles. Thereafter, the aqueous dispersion is admixed dropwise with an aqueous solution of a water-soluble cerium salt such as cerium (IV) chloride, cerium (IV) nitrate, cerium (IV) sulfate and the like while the aqueous dispersion is kept at a temperature in the range from 60° C. to 100° C. or, preferably, from 80° C. to 100° C. under agitation. The amount of the cerium salt added to the aqueous dispersion is usually in the range from 1 to 30% by weight calculated as cerium (IV) oxide $CeO_2$ based on the amount of the inorganic powder before coating contained in the aqueous dispersion.

In the next place, the aqueous dispersion of the flaky pigment particles containing the water-soluble cerium compound is admixed with a precipitant of the cerium compound so as to form and deposit a water-insoluble cerium compound, such as cerium oxide, cerium hydroxide, cerium phosphate, cerium polyphosphate, cerium carbonate, cerium oxalate and the like, on the surface of the flaky pigment particles. The precipitant should be selected depending on the particular type of the water-insoluble cerium compound to be deposited on the surface of the particles. When the desired water-insoluble cerium compound is cerium (IV) hydroxide, the pH value of the aqueous dispersion is adjusted to be in the range from 7 to 9 by the addition of a suitable pH-controlling agent, e.g. acid or alkali, in the form of an aqueous solution depending on the pH value of the aqueous dispersion before the pH adjustment so that cerium (IV) hydroxide as a water-insoluble cerium compound is formed in the aqueous dispersion and deposited on the surface of the flaky particles to form a coating layer of the water-insoluble cerium compound. When the desired water-insoluble cerium compound is cerium phosphate, the precipitant is selected from phosphoric acid and water-soluble salts thereof, polyphosphoric acid and salts thereof and the like. Similarly, cerium carbonate and cerium oxalate as a water-insoluble cerium compound can be formed by using a water-soluble carbonate, e.g., sodium carbonate, and oxalic acid or a water-soluble salt thereof, respectively, as the precipitant.

The aqueous dispersion is then filtered to give a cake of the powder which is washed with water, dried and disintegrated into a powder of flaky particles having a coating layer of the water-insoluble cerium compound although it is optional that the wet cake of the flaky particles before drying is dispersed again in an aqueous medium to be subjected to the treatment in the next step for the deposition of amorphous silica.

The cerium-coated flaky particles after drying and disintegration are then again dispersed in an aqueous medium to give an aqueous dispersion by using a suitable blending machine. The solid content in this aqueous dispersion is preferably 40% by weight or lower in order to ensure good dispersibility of the powder in the aqueous medium. In the next place, the aqueous dispersion is heated at a temperature in the range from 60° C. to 100° C. or, preferably, from 80° C. to 100° C. under agitation and an aqueous solution of a water-soluble silicate salt is added dropwise into the aqueous dispersion under agitation. Examples of suitable silicates include, in addition to inorganic silicates such as sodium silicate, organic silicate esters such as ethyl orthosilicate and the like as well as a partial hydrolysis product thereof, which can be used in the form of an aqueous emulsion. By the addition of the water-soluble or -dispersible silicate followed by the adjustment of the pH of the aqueous medium, for example, to 9 to 11, amorphous silica is formed in the aqueous dispersion and deposited on the surface of the cerium-coated flaky particles to form a composite coating layer consisting of the water-insoluble cerium compound and the amorphous silica. The amount of deposition of the amorphous silica is preferably in the range from 2 to 40% by weight calculated as silicon dioxide, $SiO_2$, based on the amount of the cerium-coated particles.

Simultaneously with or after completion of the addition of the aqueous solution of a water-soluble silicate which is alkaline as is the case with sodium silicate, the aqueous dispersion is admixed with an inorganic acid such as sulfuric acid, nitric acid and the like so as to adjust the pH of the aqueous dispersion to 9 to 11. Agitation of the aqueous dispersion for additional 30 minutes or longer is followed by neutralization with an inorganic acid so that the pH of the aqueous dispersion is brought to 6 to 7 although it is optional that the whole amount of the acid is added at a time. Thereupon, amorphous silica is deposited on the surface of the particles to complete the composite coating layer and the particles are collected by filtration, washed with water, dried and disintegrated to give flaky particles compositely coated with a water-insoluble cerium compound and amorphous silica.

The above obtained compositely coated particles are then separated from the aqueous medium of the dispersion by a suitable method such as filtration or centrifugation followed by drying. The thus dried particles are subjected to a heat treatment or calcination at a temperature in the range from 200° to 1000° C. or, preferably, from 300° to 500° C. for a length of time of at least 30 minutes.

FIG. 1 of the accompanying drawing is a graphic showing of the light transmission as a function of wavelength through a layer of the talc pigment of the compositely coated particles prepared by the above described method, of which the content of the water-insoluble cerium compound was 10% by weight calculated as $CeO_2$ based on the talc particles before coating and the content of silica was 18% by weight based on the cerium-coated talc particles. The curve I is for the powder as prepared, i.e. before heat treatment, and the curves II, III, IV and V are for the powders after a heat treatment or calcination for two hours at 150° C., 200° C., 500° C. and 1000° C., respectively. The results shown in FIG. 1 indicate that, while the powders of the compositely coated particles before heat treatment and after a heat treatment at a temperature lower than 200° C. hardly exhibit an ultraviolet-shielding effect as is shown by the curves I and II, a strong ultraviolet-shielding effect can be obtained only after a heat treatment or calcination of the compositely coated particles at a temperature of 200° C. or higher as is shown by the curves III, IV and V. Although the heat treatment or calcination was conducted on the compositely coated particles, similar ultraviolet-shielding effects can be obtained when the heat treatment or calcination is undertaken with the particles coated with a water-insoluble cerium compound alone followed by a treatment for the deposition of amorphous silica.

The procedure for the measurement of the light transmission through a layer of the powder mentioned above was as follows. Thus, 0.5 g of the sample powder and 0.4 ml of castor oil were kneaded together in a Hoover muller rotating at 50 rpm followed by the admixture of 6 ml of a clear lacquer under agitation to give a dispersion which was uniformly applied to and spread over the surface of a transparent fused quartz glass plate in a thickness of 35 μm after drying and the light transmission spectrum through the thus formed layer of the dispersion was measured by using a spectrophotometer.

In the compositely coated flaky particles of the invention, the coating amount with the water-insoluble cerium compound is in the range from 1 to 30% by weight calculated as cerium (IV) oxide based on the pigment particles before coating. When the coating amount with the cerium compound is too small, no sufficiently high ultraviolet-shielding effect can be obtained while, when the coating amount with the cerium compound is too large, the transparency or translucency of the powder to visible light is decreased to give poor appearance to the shaped articles of a plastic resin or the cosmetic composition compounded with the powder, although the ultraviolet-shielding effect can be increased so much.

Figure 2:
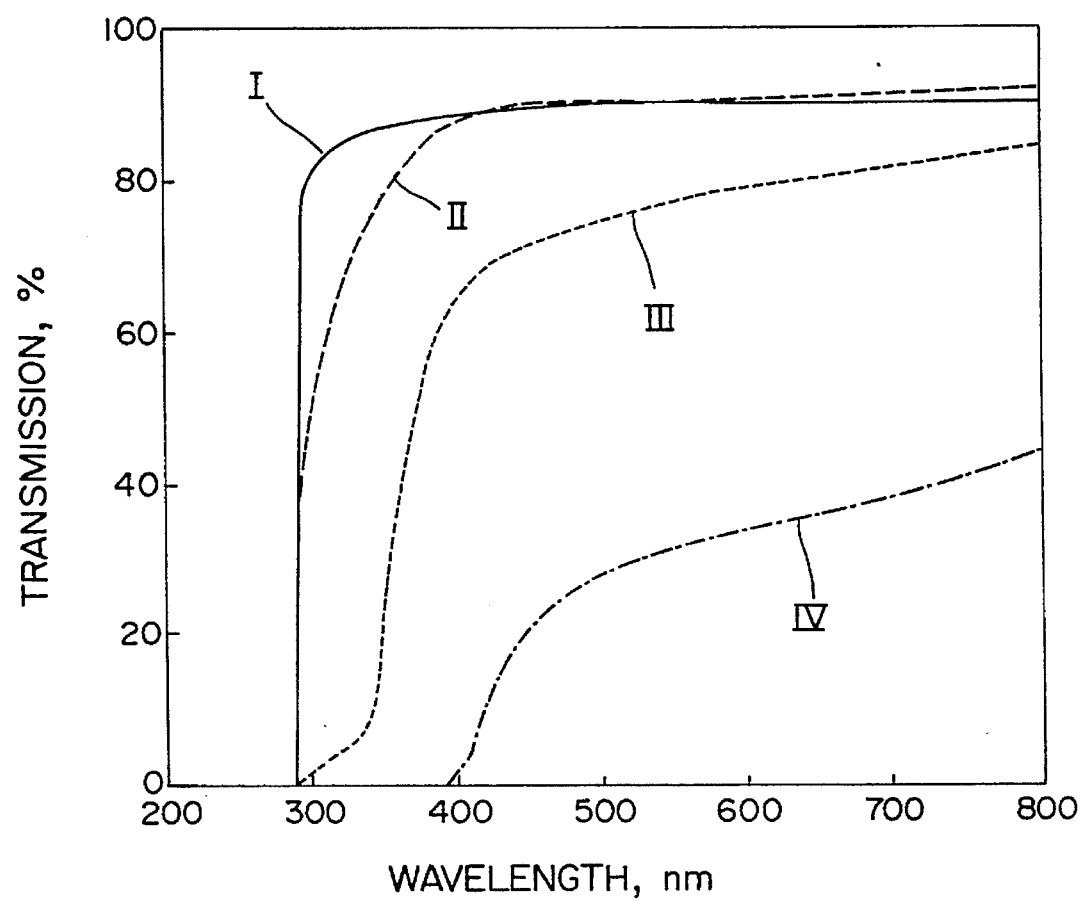
FIG. 2 is a graph showing transmission of light as a function of wavelength of light through layers of several samples of talc pigments having varied coating amounts of cerium (IV) oxide.

The above mentioned relationship is clear from FIG. 2 for a graphic showing of the light transmission through a layer of the talc powders consisting of particles coated with a water-insoluble cerium compound after a heat treatment at 500° C. for 2 hours, of which the curve I is for talc particles having no coating layer of a water-insoluble cerium compound and the curves II, III and IV are for the powders having a coating layer in a coating amount of 2%, 10% and 30% by weight, respectively, of the water-insoluble cerium compound calculated as ceriun (IV) oxide $CeO_2$ based on the talc pigment before coating.

The content of amorphous silica as a constituent of the composite coating layer on the surface of the inorganic flaky particles is in the range from 2 to 40% by weight based on the cerium-coated particles. When the amount thereof is too small, the composite coating layer after deposition of amorphous silica cannot be dense enough so that no sufficient protecting effect can be obtained for the underlying deposition of the water-insoluble cerium compound. When the content of the amorphous silica is too large, on the other hand, the deposited amorphous silica is partly in an isolated state to decrease the dispersibility of the compositely coated particles.

Figure 3:
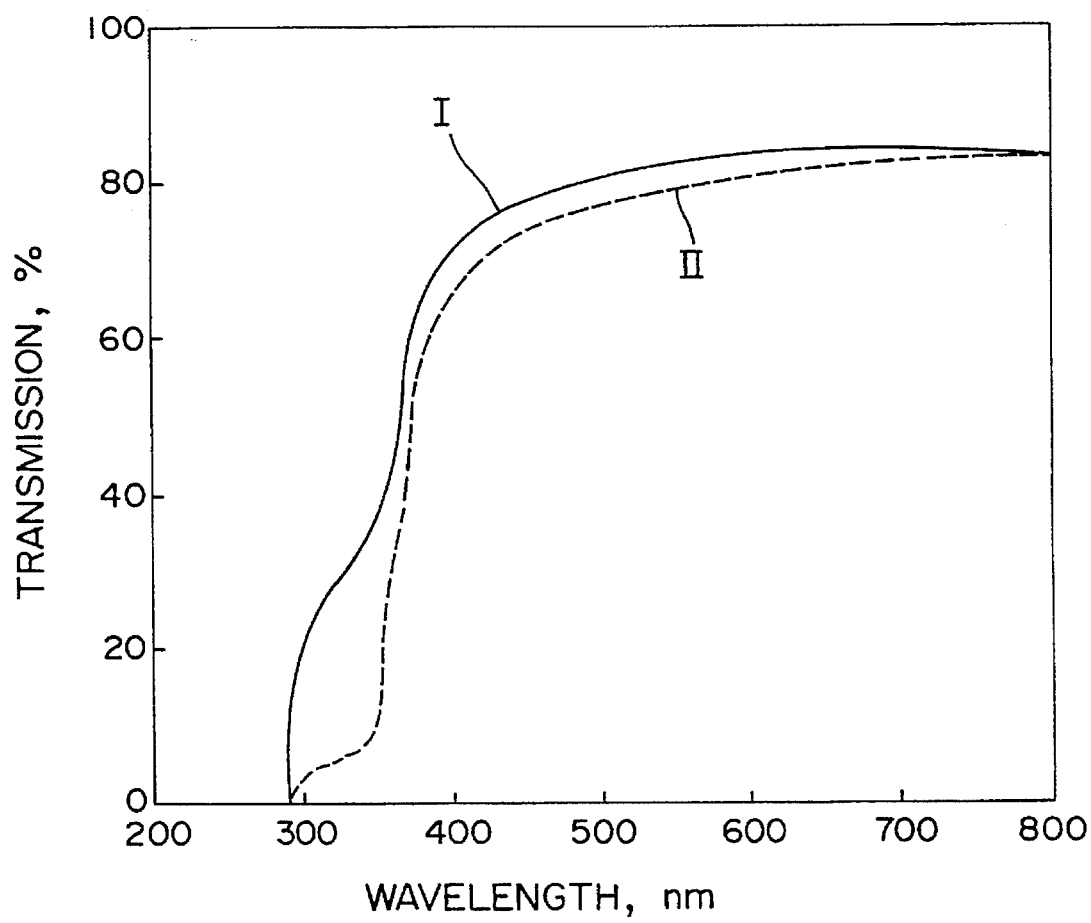
FIG. 3 is a graph showing transmission of light as a function of wavelength of light through layers of several ultraviolet-shielding agents having varied coating amounts of amorphous silica.

FIG. 3 of the accompanying drawings is a graphic showing of the light transmission through a layer of the coated talc particles after a heat treatment at 500° C. for 2 hours as a function of wavelength of the light, of which the curve I is for a powder containing 10% by weight of the water-insoluble cerium compound calculated as cerium (IV) oxide $CeO_2$ without deposition of amorphous silica and the curve II is for a powder containing 10% by weight of the water-insoluble cerium compound calculated as $CeO_2$ and 18% by weight of amorphous silica. This graph clearly indicates that the deposition treatment of amorphous silica is important in order for the particles to exhibit a high ultraviolet-shielding effect.

Figure 4:
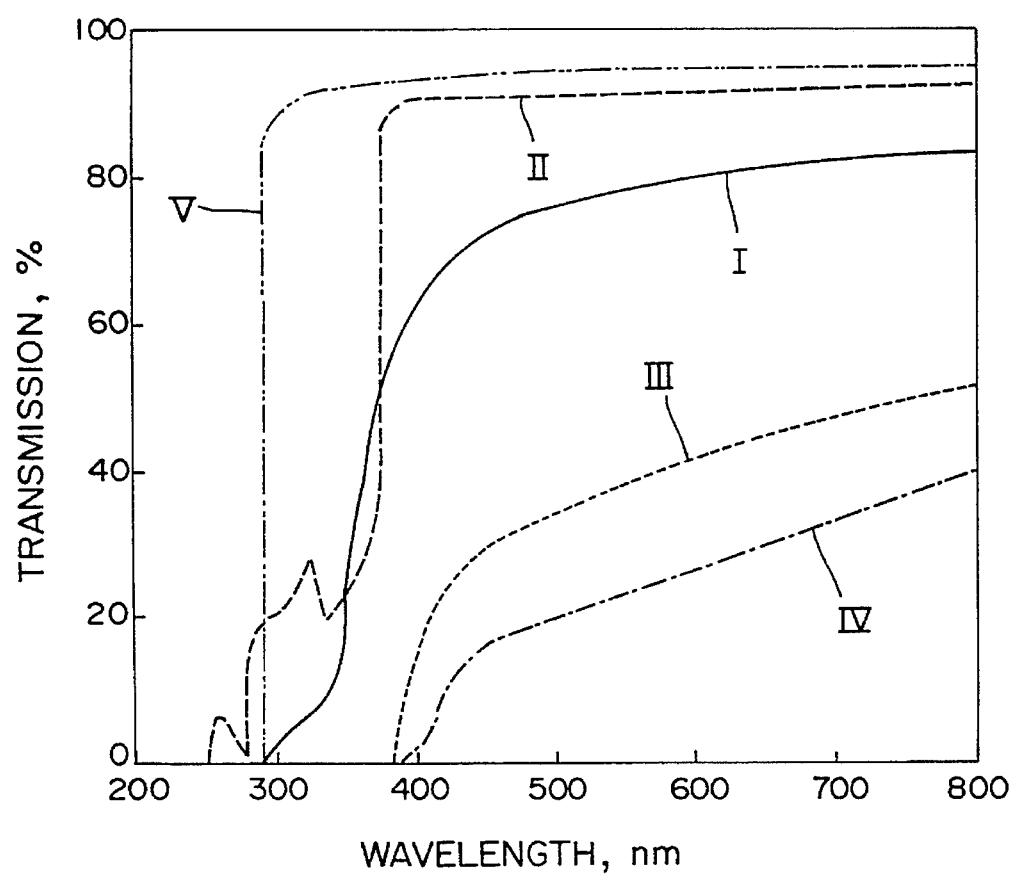
FIG. 4 is a graph showing transmission of light as a function of wavelength of light through layers of several ultraviolet-shielding agents including a talc-based inventive agent and other conventional agents.

FIG. 4 is a graphic showing of the light transmission through a layer of the inventive ultraviolet-shielding talc powder as compared with conventional ultraviolet-shielding agents, of which the curve I is for the inventive talc powder containing 10% by weight of the water-insoluble cerium compound calculated as cerium (IV) oxide and 18% by weight of amorphous silica after a heat treatment at 500° C. for 2 hours, curve II is for a conventional organic ultraviolet-shielding agent (Tinuvin 1130, a product by Ciba-Geigy Co.), curve III is for a finely divided zinc oxide powder and curve IV is for a finely divided titanium dioxide powder. The curve V is given for the purpose of control showing the absorption spectrum obtained by conducting the measurement in the same manner as for the other curves except omitting any ultraviolet-shielding agent in the sample mixture. As is understood from this figure, the ultraviolet-shielding effect of the inventive powder is superior to the organic ultraviolet-shielding agent in the wavelength region of 280 to 400 nm though somewhat inferior as compared with the conventional inorganic ultraviolet-shielding agents but, in the wavelength region of 400 to 800 nm, i.e. visible region, the light transmission of the inventive ultraviolet-shielding agent is much higher than the conventional inorganic ultraviolet-shielding agents, though somewhat lower than the organic one, indicating that better transparency or translucency could be obtained therewith when it is compounded in plastics, cosmetic compositions and the like.

As is understood from the above given description, one of the most promising applications of the inventive ultraviolet-shielding agent is as an ingredient in cosmetic or toiletry compositions desired to exhibit an ultraviolet-shielding effect for the protection of human skin against adverse influences caused by exposure to ultraviolet light. Namely, known ultraviolet-shielding agents including both organic and inorganic ones each have their own respective disadvantages and problems relative to the stability, safety, irritativeness against human skin, dispersibility, translucency and so on when they are compounded in a cosmetic composition, not to mention the expensiveness thereof as is the case with organic ultraviolet-shielding agents and insusceptibility to aesthetic coloration as is the case with synthetic micas.

In view of the above mentioned problems in the cosmetic compositions compounded with a conventional ultraviolet-shielding agent, the inventors have conducted extensive investigations leading to success in obtaining an ultraviolet-shielding cosmetic composition exhibiting unexpectedly satisfactory performance by compounding a cosmetic composition with the above described compositely coated flaky particles as an ultraviolet-shielding ingredient.

Thus, the ultraviolet-shielding cosmetic composition of the invention is a blend which comprises, in addition to at least one component with which a cosmetic composition is composed, a powder, as an ultraviolet-shielding agent, consisting of particles of an inorganic material having a refractive index of 1.45 to 1.65 and a flaky particle configuration, such as particles of mica, talc, sericite and the like, each particle being coated on the surface with a composite coating layer consisting of a water-insoluble cerium compound and amorphous silica, in an amount sufficient for the cosmetic composition to exhibit an ultraviolet-shielding effect on the human skin.

As is understood from the above given description, the ultraviolet-shielding agent used in the inventive cosmetic composition is an inorganic material so that it is free from the problem of instability as is unavoidable in conventional organic ultraviolet-absorbing or ultraviolet-shielding agents. Moreover, the particles thereof have deposition of amorphous silica so that the powder has good dispersibility in any cosmetic compositions and the cosmetic composition compounded therewith is free from the disadvantage of irritativeness against human skin. In addition, the ultraviolet-shielding agent used in the inventive cosmetic composition has high translucency to light in the visible region so that the cosmetic composition compounded therewith does not suffer from a decrease in the aesthetic value of appearance. Furthermore, the above defined ultraviolet-shielding agent used in the inventive cosmetic composition has compatibility with other ultraviolet-shielding agents so that, if desired, a cosmetic composition can be compounded with two or more kinds of ultraviolet-shielding agents in combination including the above defined one as an essential ingredient in the inventive cosmetic composition.

In the following, examples are given to illustrate the ultraviolet-shielding agent of the invention and the method for the preparation thereof as well as several formulations of the ultraviolet-shielding cosmetic compositions according to the invention. In these formulations of the cosmetic compositions, in which the term of "parts" giving the amount of the respective ingredients always refers to "parts by weight", the ultraviolet-shielding talc and mica powders, referred to as the UV-shielding talc and UV-shielding mica, respectively, were those prepared in Example 1 and Example 2, respectively.

EXAMPLE 1

An aqueous dispersion was prepared by vigorously agitating 500 g of talc in 10 liters of deionized water for one hour and 264 g of an aqueous solution of cerium (IV) nitrate in a concentration of 19% by weight calculated as cerium (IV) oxide $CeO_2$ were added dropwise into the aqueous dispersion of talc heated and kept at 80° C. under agitation. Thereafter, an aqueous solution of sodium hydroxide was added to the aqueous dispersion to adjust the pH of the aqueous dispersion to 7 to 9 so that cerium (IV) hydroxide was precipitated and deposited on the surface of talc particles to form a coating layer. The thus coated talc particles were collected by filtration, washed with water, dried and disintegrated to give a powder of flaky talc particles coated with cerium (IV) hydroxide as a water-insoluble cerium compound.

In the next place, the above obtained cerium-coated talc particles were dispersed in 10 liters of water by vigorously agitating for one hour and 348 g of sodium silicate containing 28.5% by weight of $SiO_2$ were added to the aqueous dispersion at a temperature of 80° C. or higher under agitation. The pH value of the aqueous dispersion was adjusted to 9 to 11 by the addition of diluted sulfuric acid followed by further continued agitation for additional one hour and addition of another portion of diluted sulfuric acid to adjust the pH of the aqueous dispersion to 6 to 8 so that amorphous silica was precipitated and deposited on the surface of the cerium-coated talc particles. The particles were collected by filtration, washed with water, dried and disintegrated to give a powder of flaky talc particles compositely coated with a water-insoluble cerium compound, i.e. cerium (IV) hydroxide, and amorphous silica, which was subjected to a heat treatment at 500° C. for 2 hours to give an ultraviolet-shielding agent of the invention containing 10% by weight of the water-insoluble cerium compound calculated as cerium (IV) oxide $CeO_2$ based on the talc particles before coating and 18% by weight of amorphous silica calculated as $SiO_2$ based on the ceriun-coated talc particles.

EXAMPLE 2

An aqueous dispersion was prepared by vigorously agitating 500 g of fine mica flakes in 10 liters of deionized water for one our and 527 g of an aqueous solution of cerium (IV) nitrate in a concentration of 19% by weight calculated as $CeO_2$ were added dropwise into the aqueous dispersion of mica flakes heated and kept at 80° C. under agitation followed by the adjustment of the pH value of the dispersion to 7 to 9 by the addition of an aqueous solution of sodium-carbonate so that cerium (IV) carbonate was precipitated and deposited on the surface of the mica flakes to form a coating layer of a water-insoluble cerium compound. The thus coated mica flakes were collected by filtration, washed with water, dried and disintegrated to give a powder of cerium-coated mica flakes.

The above obtained cerium-coated mica flakes were dispersed in 10 liters of deionized water by vigorously agitating for one hour and 674 g of the same sodium silicate as used in Example 1 were added to the aqueous dispersion of the cerium-coated mica flakes under agitation at a temperature of 80° C. or higher, of which the pH value was adjusted to 9 to 11 by the addition of diluted sulfuric acid and, after further continued agitation for additional one hour, to 6 to 8 by the addition of another portion of diluted sulfuric acid so that amorphous silica was precipitated and deposited on the surface of the cerium-coated mica flakes.

The thus obtained mica flakes compositely coated with a water-insoluble cerium compound and amorphous silica were collected by filtration of the aqueous dispersion, washed with water, dried and disintegrated to give a powder of the coated mica flakes, which was calcined at 900° C. for 2 hours. The thus prepared powder of compositely coated mica flakes contained the water-insoluble cerium compound and amorphous silica in amounts of 20% by weight calculated as $CeO_2$ and 32% by weight calculated as $SiO_2$, respectively, to exhibit a high and stable ultraviolet-shielding effect and translucency as in the ultraviolet-shielding agent prepared in Example 1.

Formulation of Cosmetic Composition 1

A powder foundation was prepared from each in the indicated amount of the ingredients listed below, the total amount being 100 parts:

| | | |
|---|---|---|
| (1) red iron oxide | 2.5 | parts; |
| (2) yellow iron oxide | 2.0 | parts; |
| (3) black iron oxide; | 0.2 | part; |
| (4) titanium dioxide | 15.0 | parts; |
| (5) UV-shielding mica | 20.0 | parts; |
| (6) UV-shielding talc | 50.6 | parts; |
| (7) liquid paraffin | 4.5 | parts; |
| (8) octyl dodecyl myristate | 3.0 | parts; |
| (9) petrolatum and | 2.0 | parts; |
| (10) p-hydroxybenzoic acid | 0.2 | part. |

Thus, the ingredients (1) to (6) were first mixed together and the mixture was transferred into a high-speed blender followed by the admixture of the ingredients (7) to (10) to be thoroughly blended. The thus prepared uniform mixture was disintegrated by using a pulverizing machine followed by particle size classification by using a set of screens. The powder could be readily shaped by compression molding into a compact cake.

Formulation of Cosmetic Composition 2

A water-type powder foundation was prepared from each in the indicated amount of the ingredients listed below, the total amount being 100 parts:

| | | |
|---|---|---|
| (1) titanium dioxide | 10.0 | parts; |
| (2) colloidal kaolin | 25.0 | parts; |
| (3) UV-shielding talc | 45.3 | parts; |

-continued

| | | |
|---|---|---|
| (4) red iron oxide | 0.9 | part; |
| (5) yellow iron oxide | 3.0 | parts; |
| (6) black iron oxide; | 0.1 | part; |
| (7) liquid paraffin | 9.0 | parts; |
| (8) sorbitan sesquioleate | 4.0 | parts; |
| (9) glycerin and | 2.5 | parts; |
| (10) methyl p-oxybenzoate | 0.2 | part. |

Thus, the ingredients (1) to (6) were first mixed together and the mixture was transferred into a high-speed blender followed by the addition of the ingredient (9) to be blended. Thereafter, the ingredients (7), (8) and (10) were added to the blender in which they were thoroughly blended together. The thus prepared uniform mixture was disintegrated by using a pulverizing machine followed by particle size classification by using a set of screens. The powder could be readily shaped by compression molding into a compact cake.

Formulation of Cosmetic Composition 3

A liquid foundation was prepared from each in the indicated amount of the ingredients listed below, the total amount being 100 parts:

| | | |
|---|---|---|
| (1) stearic acid | 2.5 | parts; |
| (2) propyleneglycol monostearate | 2.0 | parts; |
| (3) cetanol | 0.3 | part; |
| (4) liquid lanolin | 2.0 | parts; |
| (5) liquid paraffin | 2.5 | parts; |
| (6) isopropyl myristate | 7.0 | parts; |
| (7) propyl p-oxybenzoate | 0.1 | part; |
| (8) purified water | 59.9 | parts; |
| (9) sodium carboxymethyl cellulose | 0.2 | part; |
| (10) bentonite | 0.5 | part; |
| (11) 1,3-butyleneglycol | 5.0 | parts; |
| (12) triethanolamine | 1.2 | parts; |
| (13) methyl p-oxybenzoate | 0.2 | part; |
| (14) titanium dioxide | 8.5 | parts; |
| (15) UV-shielding talc | 4.5 | parts; |
| (16) red iron oxide | 2.0 | parts; |
| (17) yellow iron oxide and | 1.5 | parts; |
| (18) black iron oxide | 0.1 | part. |

The procedure for the preparation was as follows.

[I] The ingredients (14) to (18) were mixed together to form a mixture.

[II] The ingredient (10) was added to (8) to be fully swollen at 70 ° C. followed by the admixture of a dispersion of the ingredients (9) and (11) to be dissolved followed by the further addition of the ingredients (12) and (13).

[III] The ingredients (1) to (7) were heated together at 70° to 80° C. to giveas an oily phase.

[IV] The mixture prepared in [I] was added to the mixture prepared in [II] and the resultant mixture was passed through a colloid mill to give an aqueous phase.

[V] The aqueous phase prepared in [IV] was heated at 75° C. and admixed with the oily phase heated at 80° C. to effect emulsification followed by cooling under continued agitation down to 30° C.

Formulation of Cosmetic Composition 4

A cream foundation was prepared from each in the indicated amount of the ingredients listed below, the total amount being 100 parts:

| | | |
|---|---|---|
| (1) stearic acid | 5.0 | parts; |
| (2) oleophilic glycerin monostearate | 2.5 | parts; |
| (3) cetanol | 1.5 | parts; |
| (4) propyleneglycol monolaurate | 2.5 | parts; |
| (5) liquid paraffin | 8.0 | parts; |
| (6) isopropyl myristate | 7.0 | parts; |
| (7) propyl p-oxybenzoate | 0.1 | part; |
| (8) purified water | 47.3 | parts; |
| (9) triethanolamine | 1.2 | parts; |
| (10) sorbitol | 3.0 | parts; |
| (11) methyl p-oxybenzoate | 0.2 | part; |
| (12) titanium dioxide | 8.0 | parts; |
| (13) kaolin | 5.0 | parts; |
| (14) UV-shielding talc | 3.0 | parts; |
| (15) bentonite | 1.0 | part; |
| (16) red iron oxide | 2.5 | parts; |
| (17) yellow iron oxide and | 2.0 | parts; |
| (18) black iron oxide | 0.2 | part. |

The procedure for the preparation was as follows.

[I] The ingredients (12) to (14) and (16) to (18) were mixed together to form a mixture.

[II] The ingredient (15) was added to (8) to be fully swollen at 80 ° C. followed by the admixture of the ingredients (9) to (11 ) to be dissolved. The thus obtained mixture was admixed with the mixture prepared in [I] above to give an aqueous phase, which was kept at 80° C.

[III] The ingredients (1) to (7) were heated together at 80° C. to give an oily phase.

[IV] The aqueous phase prepared in [II] was admixed with the oily phase to effect emulsification followed by cooling under continued agitation down to 35° C.

Formulation of Cosmetic Composition 5

A sun-screen lotion was prepared from each in the indicated amount of the ingredients listed below, the total amount being 100 parts:

| | | |
|---|---|---|
| (1) stearic acid | 4.0 | parts; |
| (2) cetanol | 1.0 | part; |
| (3) glyceryl trioctoate | 6.0 | parts; |
| (4) octyl methoxycinnamate | 6.0 | parts; |
| (5) vitamin E acetate | 1.0 | part; |
| (6) dimethylpolysiloxane | 0.5 | part; |
| (7) octyl p-(dimethylamino)benzoate | 1.5 | parts; |
| (8) propyl p-oxybenzoate | 0.1 | part; |
| (9) self-emulsifiable glycerin monostearate | 2.0 | parts; |
| (10) purified water | 69.53 | parts; |
| (11) propyleneglycol | 5.0 | parts; |
| (12) sodium hydroxide | 0.15 | part; |
| (13) tetrasodium edetate | 0.1 | part; |
| (14) carboxyvinyl polymer and | 0.12 | part; |
| (15) UV-shielding talc | 3.0 | parts. |

The procedure for the preparation was as follows.

[I] The ingredients (1) to (9) were mixed together and dissolved by heating at 80° C. to give an oily phase.

[II] The ingredient (14) was added to (10) and dissolved therein followed by the admixture of the ingredients (11) to (13) to be dissolved. The thus obtained mixture was further admixed with the ingredient (15) and heated at 80° C. to give a uniform dispersion as an aqueous phase.

[III] The aqueous phase prepared in [II] was admixed with the oily phase to effect emulsification followed by cooling under continued agitation down to 40° C.

Formulation of Cosmetic Composition 6

A sun-protect cream was prepared from each in the indicated amount of the ingredients listed below, the total amount being 100 parts:

| | | |
|---|---|---|
| (1) self-emulsifiable glycerin monostearate | 6.0 | parts; |
| (2) camellia oil | 4.0 | parts; |
| (3) glyceryl trioctoate | 7.0 | parts; |
| (4) behenyl alcohol | 3.5 | parts; |
| (5) UV-shielding talc | 8.0 | parts; |
| (6) octyl dodecyl myristate | 2.5 | parts; |
| (7) stearic acid | 2.0 | parts; |
| (8) propyl p-oxybenzoate | 0.1 | part; |
| (9) purified water | 66.4 | parts; |
| (10) carboxyvinyl polymer | 0.2 | part; |
| (11) methyl p-oxybenzoate and | 0.2 | part; |
| (12) triethanolamine | 0.1 | part. |

The procedure for the preparation was as follows.

[I] The ingredients (1) to (8) were mixed together and dissolved by heating at 80° C. to give an oily phase.

[II] The ingredient (9) was added to (10) and dissolved therein followed by the admixture of the ingredients (11) and (12) to give an aqueous phase which was heated at 80° C.

[III] The aqueous phase prepared in [II] was admixed with the oily phase to effect emulsification followed by cooling under continued agitation down to 37° C.

Formulation of Cosmetic Composition 7

A sun-screen cream was prepared from each in the indicated amount of the ingredients listed below, the total amount being 100 parts:

| | | |
|---|---|---|
| (1) self-emulsifiable glycerin monostearate | 9.0 | parts; |
| (2) olive oil | 8.0 | parts; |
| (3) cetyl palmitate | 4.5 | parts; |
| (4) behenyl alcohol | 2.0 | parts; |
| (5) octyl p-(dimethylamino)benzoate | 3.0 | parts; |
| (6) UV-shielding talc | 5.0 | parts; |
| (7) propyl p-oxybenzoate | 0.1 | part; |
| (8) purified water | 67.85 | parts; |
| (9) carboxyvinyl polymer | 0.25 | part; |
| (10) methyl p-oxybenzoate and | 0.2 | part; |
| (11) triethanolamine | 0.1 | part. |

The procedure for the preparation was as follows.

[I] The ingredients (1) to (7) were mixed together and dissolved by heating at 80° C. to give an oily phase.

[II] The ingredient (9) was added to (8) and dissolved therein followed by the admixture of the ingredients (10) and (11) to give an aqueous phase which was heated at 80° C.

[III] The aqueous phase prepared in [II] was admixed with the oily phase to effect emulsification followed by cooling under continued agitation down to 35° C.

What is claimed is:

1. A method for the preparation of an inorganic ultraviolet-shielding agent in a powdery form which comprises the steps of:

(A) dispersing particles of an inorganic material having a refractive index in the range from 1.45 to 1.65 and a flaky particle configuration selected from the group consisting of mica, talc and sericite in an aqueous medium to prepare an aqueous dispersion;

(B) adding, to the aqueous dispersion prepared in step (A) above, an aqueous solution of a water-soluble cerium compound;

(C) adding a precipitant of the cerium compound to the aqueous dispersion of the inorganic particles containing the water-soluble cerium compound so as to deposit a water-insoluble cerium compound selected from the group consisting of cerium oxide, cerium hydroxide, cerium phosphate, cerium polyphosphate, cerium carbonate and cerium oxalate on the surface of the particles;

(D) adding, to the aqueous dispersion of the inorganic particles having the water-insoluble cerium compound deposited on the surface thereof prepared in step (C), an aqueous solution of a water-soluble or water-dispersible silicate compound;

(E) adjusting the pH of the aqueous dispersion to 9 to 11 so as to deposit amorphous silica on the surface of the particles to form a composite coating layer consisting of the water-insoluble cerium compound and the amorphous silica;

(F) separating the particles from the aqueous medium of the dispersion followed by drying; and (G) calcining the dried particles at a temperature in the range from 200° to 1000° C.

2. The method for the preparation of an inorganic ultraviolet-shielding agent in a powdery form as claimed in claim 1 in which the precipitant added to the aqueous dispersion of the particles is an acid or alkali in an amount sufficient to adjust the pH of the aqueous dispersion to 7 to 9.

3. The method for the preparation of an inorganic ultraviolet-shielding agent in a powdery form as claimed in claim 1 in which the temperature of the aqueous dispersion in step (B) is in the range from 60° to 100° C.

4. The method for the preparation of an inorganic ultraviolet-shielding agent in a powdery form as claimed in claim 1 in which the amount of the water-soluble cerium compound added in step (B) is in the range from 1 to 30% by weight calculated as cerium (IV) oxide based on the amount of the particles of the inorganic material.

5. The method for the preparation of an inorganic ultraviolet-shielding agent in a powdery form as claimed in claim 1 in which the amount of the water-soluble or water-dispersible silicate compound added in step (C) is in the range from 2 to 40% by weight calculated as silicon dioxide based on the total amount of the particles of the inorganic material and the water-insoluble cerium compound calculated as cerium (IV) oxide.

6. The method for the preparation of an inorganic ultraviolet-shielding agent in a powdery form as claimed in claim 1 in which the water-soluble or water-dispersible silicate is sodium silicate.

7. The method as in claim 1, wherein the aqueous dispersion prepared in step (A) is maintained at a temperature in the range from 80° to 100° C. during addition of the aqueous solution of a water-soluble cerium compound in step (B).

* * * * *